(12) United States Patent
Kohn Bitran

(10) Patent No.: US 9,215,977 B2
(45) Date of Patent: Dec. 22, 2015

(54) PORTABLE DEVICE FOR INDIRECT OPHTHALMOLOGY

(71) Applicant: David Kohn Bitran, Santiago (CL)

(72) Inventor: David Kohn Bitran, Santiago (CL)

( * ) Notice: Subject to any disclaimer, the term of this patent is extended or adjusted under 35 U.S.C. 154(b) by 99 days.

(21) Appl. No.: 13/849,552

(22) Filed: Mar. 25, 2013

(65) Prior Publication Data

US 2014/0285766 A1 Sep. 25, 2014

(51) Int. Cl.
*A61B 3/14* (2006.01)
*A61B 3/10* (2006.01)
*A61B 3/00* (2006.01)

(52) U.S. Cl.
CPC ............... *A61B 3/14* (2013.01); *A61B 3/0025* (2013.01); *A61B 3/0075* (2013.01)

(58) Field of Classification Search
CPC .......... A61B 3/12; A61B 3/1208; A61B 3/13; A61B 3/14; A61B 3/145; A61B 5/0013; A61B 5/6803; A61B 3/10; A61B 3/0008; G02B 21/0012; G02B 21/362; H04N 5/2251
USPC ......... 351/200, 205, 206, 221, 243, 246, 208, 351/218, 213, 214; 396/18; 348/78, 345, 348/373
See application file for complete search history.

(56) References Cited

U.S. PATENT DOCUMENTS

| | | | | |
|---|---|---|---|---|
| 3,586,424 A * | 6/1971 | Schenk et al. | ............... | 351/213 |
| 3,881,812 A * | 5/1975 | Ben-Tovim | ................ | 351/205 |
| 4,856,892 A * | 8/1989 | Ben-Tovim | ................ | 351/218 |
| 5,020,323 A * | 6/1991 | Hurlimann | ................ | 60/413 |
| 5,589,896 A * | 12/1996 | Mainster et al. | ............. | 351/219 |
| 5,943,116 A * | 8/1999 | Zeimer | ................... | 351/221 |
| 6,390,625 B1 * | 5/2002 | Slawson et al. | ............. | 351/216 |
| 6,409,343 B1 * | 6/2002 | Uchida | ...................... | 351/208 |
| 7,802,884 B2 | 9/2010 | Feldon et al. | | |
| 8,337,017 B2 | 12/2012 | Goldfain et al. | | |
| 8,353,595 B2 | 1/2013 | Mann | | |
| 8,704,944 B1 * | 4/2014 | Wierzoch et al. | ............. | 348/375 |
| 2005/0270484 A1 * | 12/2005 | Maeda et al. | ................ | 351/206 |

(Continued)

OTHER PUBLICATIONS

Wendy W. Lee. Slit Lamp Adapters turn Smartphones into Clinical Cameras. https://web.archive.org/web/20150318025532/http://www.ophthalmologyweb.com/Featured-Articles/136817-Slit-Lamp-Adapters-turn-Smartphones-into-Clinical-Cameras/, May 14, 2013.*

(Continued)

*Primary Examiner* — Zachary Wilkes
*Assistant Examiner* — Collin X Beatty
(74) *Attorney, Agent, or Firm* — Soroker-Agmon

(57) ABSTRACT

A device for examining an eye of a subject including a camera detachably mounted on a camera mounting unit. The camera includes an illuminating source, which generates illuminating radiation for irradiating the eye thereby enabling the camera to generate a plurality of images of the eye. The device also includes a first lens assembly detachably mounted on an adjustable lens holder and selected to focus the illuminating radiation towards the eye as well as focusing radiation reflected from the eye towards an entrance pupil of the camera. An extendible support arm supports the camera and the adjustable lens holder at a first distance between the camera and the first lens assembly. Subsequent to adjusting the first distance to correspond to a diopter value of the selected first lens assembly, the illuminating source irradiates the eye and subsequent thereto the camera generates the plurality of images of the eye.

19 Claims, 4 Drawing Sheets

(56) References Cited

U.S. PATENT DOCUMENTS

| | | | |
|---|---|---|---|
| 2008/0316427 A1* | 12/2008 | Fisher et al. | 351/233 |
| 2011/0085138 A1* | 4/2011 | Filar | 351/206 |
| 2012/0200690 A1* | 8/2012 | Beasley | 348/78 |
| 2012/0287255 A1* | 11/2012 | Ignatovich et al. | 348/78 |
| 2012/0320340 A1* | 12/2012 | Coleman, III | 351/208 |
| 2013/0033593 A1* | 2/2013 | Chinnock et al. | 348/78 |
| 2013/0083185 A1* | 4/2013 | Coleman, III | 348/78 |
| 2013/0100271 A1* | 4/2013 | Howes | 348/78 |
| 2013/0128223 A1* | 5/2013 | Wood et al. | 351/206 |
| 2013/0169934 A1* | 7/2013 | Verdooner | 351/246 |
| 2013/0182217 A1* | 7/2013 | Cheng et al. | 351/206 |

OTHER PUBLICATIONS

Jay Chhablani, Simon Kaja, and Vinay A. Shah. Smartphones in ophthalmology. Indian J Ophthalmol, Mar.-Apr. 2012; 60(2): 127-131. doi: 10.4103/0301-4738.94054.*

* cited by examiner

PORTABLE DEVICE FOR INDIRECT OPHTHALMOLOGY

FIELD OF THE INVENTION

The present invention relates to the field of indirect ophthalmology.

BACKGROUND OF THE INVENTION

Pathology of the eye, such as optic nerve changes, eye hemorrhages, blood vessel abnormalities and pigmentation, can be detected by an ophthalmologist observing different portions of the eye fundus. Current ophthalmoscope devices photograph portions of the eye for diagnosing retinal diseases and monitoring progression of disease. In addition, current ophthalmoscope devices provide a reference image for future consultations.

Current indirect ophthalmoscope devices are cumbersome and bulky and are not amenable for use.

SUMMARY OF THE INVENTION

The current invention relates to an indirect ophthalmoscope device which enables an ophthalmologist to study a selected portion of an eye of a subject. The present invention includes, inter alia, a camera and an illuminating source associated with a lens assembly. The illuminating source illuminates an at least one eye portion requiring medical examination and the camera generates a plurality of images of the at least one eye portion, for on-line and/or off-line examination.

Preferably, the camera and the illuminating source are integrally constructed, such as in a mobile phone, for example, an iPhone®. Thus, the present invention is portable and handheld and thus amenable for medical examination of the eye of the subject.

The diopter value of the lens assembly is selected in accordance with medical requirements for examining the selected at least one portion of the eye. The camera and illuminating source and the lens assembly are supported by an extendible support arm. The extendible support arm enables the ophthalmologist to vary the distance between the camera and the illuminating source and the lens assembly thereby enabling different lens assemblies to be selected in accordance with medical requirements.

The current invention is handheld and portable and generates high quality images of the area of interest of the eye. The current invention typically uses the photographic capabilities of a mobile phone, such as an iPhone®, a Smartphone®, Samsung Galaxy®, Android phone® and point-shoot cameras. By integrating the mobility and high quality photographic capabilities of a mobile phone with an appropriate lens assembly, a portable device of low cost and high efficiency is achieved. The current invention generates high quality images of various portions of the eye as required by the ophthalmologist.

There is provided in accordance with an embodiment of the present invention, a device for examining at least one selected portion of an eye of a subject, including a camera detachably mounted on a camera mounting unit and including an illuminating source being operable to generate illuminating radiation for irradiating the at least one portion of the eye thereby enabling the camera to generate a plurality of images of the at least one portion of the eye, a first lens assembly detachably mounted on an adjustable lens holder and selected to focus the illuminating radiation towards the at least one portion of the eye and focus radiation reflected from the at least one portion of the eye towards an entrance pupil of the camera, and an extendible support arm having a proximal end and a distal end and being operable to support the camera mounting unit at the proximal end and the adjustable lens holder at the distal end at a first distance between the camera and the first lens assembly. Subsequent to adjusting the first distance to correspond to a diopter value of the selected first lens assembly, by means of an adjusting unit associated with the extendible support arm, the illuminating source is operably configured to irradiate the at least one portion of the eye and subsequent thereto the camera is operably configured to generate the plurality of images of the at least one portion of the eye.

Further in accordance with an embodiment of the present invention, the illumination source is located on a front panel of the camera.

Still further in accordance with an embodiment of the present invention, the illumination source and the entrance pupil of the camera are located within a field-of-view of the selected first lens assembly.

Additionally, the adjusting unit is configured to adjust the first distance.

Moreover Further in accordance with an embodiment of the present invention, the first distance is in a range of approximately 3 cms to 10 cms.

Further in accordance with an embodiment of the present invention, the extendible support arm includes a telescopic support arm.

Still further in accordance with an embodiment of the present invention, the first lens assembly includes at least one focusing lens.

Additionally in accordance with an embodiment of the present invention, the diopter value is in a range of approximately 10 diopters to 40 diopters.

Further in accordance with an embodiment of the present invention, the selected first lens assembly has a diameter in a range of approximately 3 cms to 10 cms.

Still further in accordance with an embodiment of the present invention, further including a second lens assembly located in proximity to the entrance pupil of the camera and including at least one magnifying lens configured to magnify the reflected radiation. Typically, the second lens assembly includes at least one magnifying lens.

Typically, the camera is a portable camera.

Further in accordance with an embodiment of the present invention, the camera and the illuminating source are integrated in a mobile phone.

Still further in accordance with an embodiment of the present invention, the camera includes a computer readable storage medium including a menu of instructions for operating the device, the menu of instructions includes operating the illuminating source to irradiate the at least one portion of the eye, activating the camera to generate the plurality of images of the at least portion of the eye, comparing at least two eye images of the plurality of images for detecting eye changes in pathology of the eye, merging the at least two eye images of the plurality for detecting eye changes in pathology of the eye storing the at least one image of the plurality of images.

Additionally in accordance with an embodiment of the present invention, the camera further includes a storage area for storing subject information.

Further in accordance with an embodiment of the present invention, an extendible and retractable arm integrally located in the extendible support arm and configured to stabilize the device against the forehead of the subject during a medical procedure.

Further in accordance with an embodiment of the present invention, the adjusting unit includes an outer sleeve having a first set of geared teeth associated with an inner surface of the outer sleeve, an inner sleeve having a second set of geared teeth associated with an outer surface of the inner sleeve and the second set of geared teeth is configured to engage the first set of geared teeth, and a dial rotatably attached. to the inner sleeve. The dial is operably configured to laterally displace the inner sleeve within the outer sleeve by the first set of geared teeth engaging the second set of geared teeth, thereby the adjusting unit adjusts the first distance.

Still further in accordance with an embodiment of the present invention, the adjusting unit includes an outer sleeve having a first frictional coating associated with an inner surface of the outer sleeve, and an inner sleeve having a second frictional coating associated with an outer surface of the inner sleeve and the second frictional coating is configured to frictionally engage the first frictional coating. Upon laterally displacing the inner sleeve within the outer sleeve by the frictional engagement between the first frictional coating and the second frictional coating, the adjusting unit adjusts the first distance.

BRIEF DESCRIPTION OF THE DRAWINGS

A preferred embodiment of the current invention is described hereinbelow with reference to the following drawings.

DETAILED DESCRIPTION OF AN EMBODIMENT OF THE PRESENT INVENTION

Figure 1:
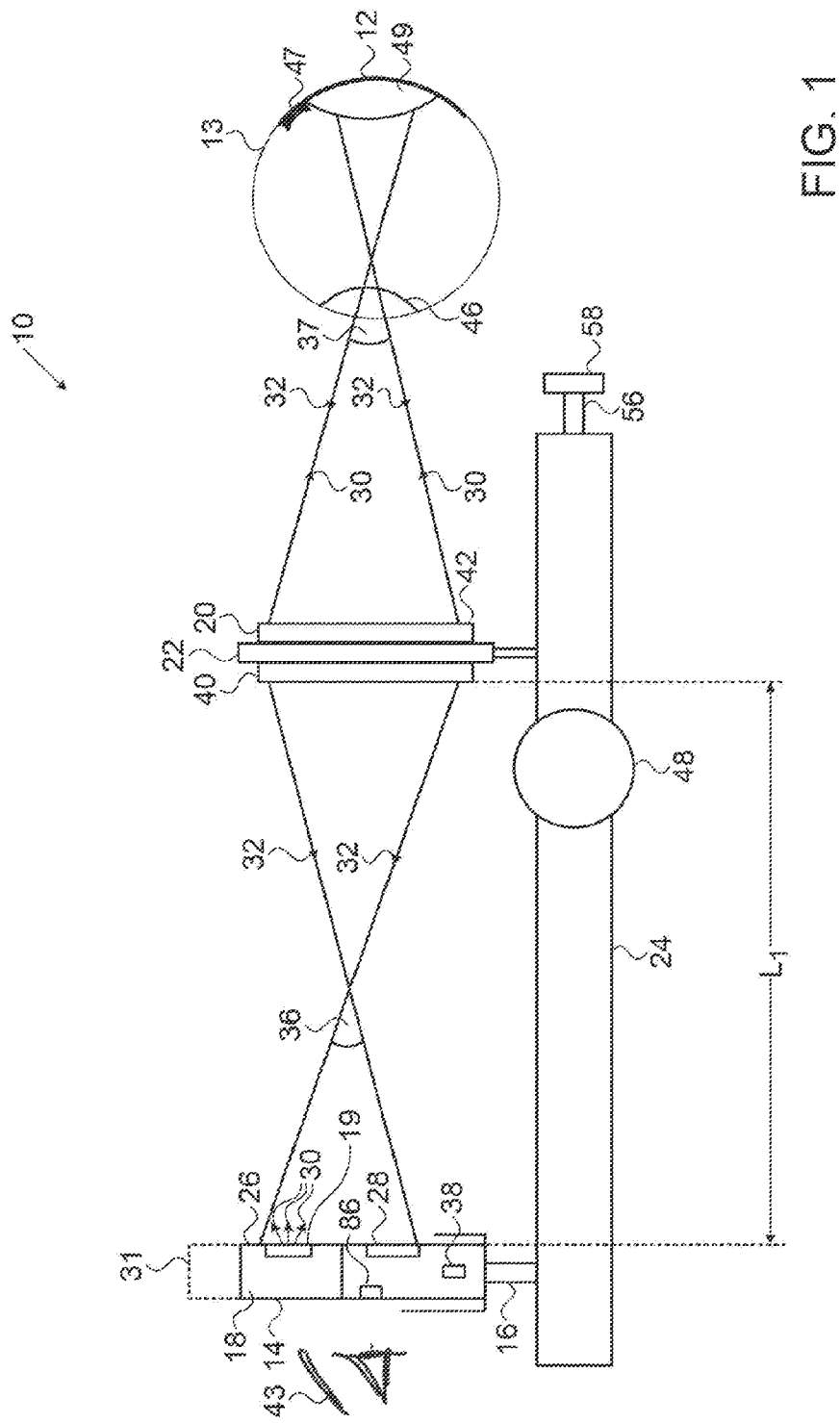
FIG. 1 schematically presents a device for examining at least one eye portion of an eye of a subject, constructed and operative in accordance with an embodiment of the present invention.

Reference is now made to FIG. 1, which schematically presents an ophthalmoscope device 10 for examining a selected at least one eye portion 12 of an eye 13 of a subject, constructed and operative in accordance with an embodiment of the present invention. The device 10 includes, inter alia, a camera 14 detachably mounted on a camera mounting unit 16 and a first lens assembly 20 detachably mounted on an adjustable lens holder 22. The camera mounting, unit 16 and the adjustable lens holder 22 are supported by an extendible support arm 24.

The camera 14 is detachably mounted on the camera mounting unit 16 and includes, inter alia. an illuminating source 18, which generates illuminating radiation 30 for irradiating the selected at least one portion 12 of the eye 13. The camera 14 is interchangeable enabling the ophthalmologist to exchange cameras according to requirements, such as sensitivity requirements of the images of the at least one eye portion 12 of the eve 13. The first lens assembly 20 focuses the illuminating. radiation 30, winch falls within a first field-of-view 36, onto the at least one eye portion 12. Reflected radiation 32 from the at least one eve portion 12 is focused by the lens assembly 20 onto an entrance pupil 28 of the camera 14, thereby enabling the camera 14 to generate a plurality of images of the selected at least one eve portion 2 of the eve 13. The illuminating radiation 30 and the reflected radiation 32 pass through the pupil 46 of the eye 13, as is known in the art.

The illuminating source 18 is preferably located on a front panel 26 of the camera 14 in proximity to the entrance pupil 28 of the camera 14, such that the entrance pupil 28 and the illuminating source 18 are located within the first field-of-view 36 of the lens assembly 20. Typically, the illuminating source operates in the optical wavelength range of approximately 400 nm to 700 nm.

The camera 14 is detachably mounted on the camera mounting unit 16 enabling the camera 14 to be interchangeable with different appropriate cameras in which the illuminating source 18 and the entrance pupil 28 are located within the first field-of-view 36 of the lens assembly 20.

The illuminating source 18 generates the illuminating radiation 30 for illuminating the at least one eye portion 12. As described below, in order to reduce the intensity of the irradiating radiation as well as facilitating examination of different portions of the eye, various types of filters are located in front of the illuminating source 18 and the camera 14, as described below.

The lens assembly 20 includes, inter alia, at least a first lens group 40 and a second lens group 42. Typically, the lens assembly 20 is asymmetric. The first lens group 40 has a focal length $f_1$ and the first field-of-view 36 and the second lens group 42 has a focal length $f_2$ and a second field-of-view 37.

The lens assembly 20 is detachably mounted on the adjustable lens bolder 22 thereby enabling exchanging the lens assembly 20 in accordance with medical requirements for the examination of the eye 13. Typically, the power of the lens assembly 20 is selected as to enable observation and examination of an area of interest 49 of the selected at least one eve portion 12 the fundus 47 of the eye 13.

A typical range of lens power used for eye examination ranges from about 14D to about 40D, as is known in the art. Preferably, a lens assembly 20 having a lens power of 20D are selected. Typically, the 20D lens assembly has a diameter of approximately 5.5 cms and a field-of-view with a range of approximately 46°-60°. The 28D lens, typically, has a diameter of approximately 4.5 cms and a field-of-view with a range of approximately 53°-69°. The 20D lens has a value of $f_1$ of 5 cms. and the 28D lens has a value of $f_1$ of 3.5 cms.

Lenses of various diameters are supported in the lens holder 22 by appropriately adjusting support arms of the lens holder 22 (not shown), as is known in the art. The adjustable lens holder 22 enables exchanging lens assemblies with lenses of various diameters and thicknesses, in accordance with the medical requirements.

The extendible support arm 24 supports the camera mounting unit 16 and the adjustable lens holder 22 so as to maintain a distance $L_1$ between the entrance pupil 28 and the first lens group 40. Typically, $L_1 \approx 2f_1$. Due to differences in the lens power and focal lengths of the lens assembly 20 required for observing and examining different areas of interest of the eye 13, an adjusting unit 48 is located in the extendible support arm 24 and is constructed and operative to adjust the first distance $L_1$, as described below.

The adjusting capability of the extendible support arm 24 enables a user 43 to focus and illuminate different areas of interest 49 of the eye fundus 47 and generate the corresponding plurality of images of the area of interest 49, in accordance with medical requirements.

A typical camera 14 and illuminating source S fulfilling, for example, a condition of being within the first field-of-view 36, are typically the integrated camera and illuminating source of a mobile phone 31, such as an iPhone. RTM. In the iPhone. RTM, a distance between the entrance pupil 28 and the illuminating source 18 typically 7.5 mm. Integrating the mobile phone 31 with the lens assembly 20 provides a portable ophthalmoscope device of low cost and high efficiency for generating high quality images of different portions Of the eye.

In accordance with some embodiments of the present invention, the present invention is operable with an external illuminating source, which is not integrally constructed with the camera 14 of the mobile phone 31. It is appreciated that in these embodiments, appropriate optical devices, such as requisite prisms and lenses, are required to direct the illuminating radiation 30 towards the at least one eye portion 12.

The dimensions and geometry of the camera mounting unit 16 are selected to conform to the dimensions and geometry of the mobile phone 31 and/or the camera and the illuminating source, if an external illuminating source is used. Thus, the ophthalmologist is able to select and operate the mobile phone 31 and/or camera and external illuminating source, which fulfills the medical requirements.

It is appreciated that the camera mounting unit 16 is constructed to conform to the dimensions and geometry of each selected mobile phone 31. Alternatively, the camera mounting unit 16 has variable dimensions and geometry in order to conform to the selected mobile phone 31.

It is further appreciated that if the external illuminating source is used, the camera mounting unit 16 is constructed to conform to the dimensions and geometry of the camera and the external illuminating source and the complementary optical devices, as described above.

The camera 14 is programmable, as known in the art, enabling various functionalities for generating and analyzing the generated plurality of images of the at least one potion 12 of the eye. Applications for fulfilling these functionalities include, inter alia, instructions for: forwarding instructions to the mobile phone 31 to operate the illuminating source 18; operating the camera 14 to generate the plurality of images of the at least open eye portion 12; analyzing each image of the plurality of images on-line; storing the plurality of images of the at least portion of the eye for analysis of the plurality of images off-line; comparing at least two eye images of the plurality of images for detecting eye changes in pathology of the eye and merging the at least two eye images of the plurality for detecting eye changes in pathology of the eye.

The functionalities of the camera 14 enable the user 43 to observe and analyze each one of the plurality of images of the eye portion 12 in real-time or stored in a memory 38 of the mobile phone 31 for analysis by the user 43 at a later time.

An extendible and retractable arm 56, typically the arm is manually operated, is attached to the extendible support arm 24. The extendible and retractable arm 56 enables the user 43 to stabilize the device 10 during a medical procedure. The arm 56 includes, inter alia, an abutment unit 58 for abutting the arm 56 against the forehead of the patient, as described below.

In some embodiments, the extendible and retractable arm 56 is operated by a motor, such as an electric motor.

Figure 2:
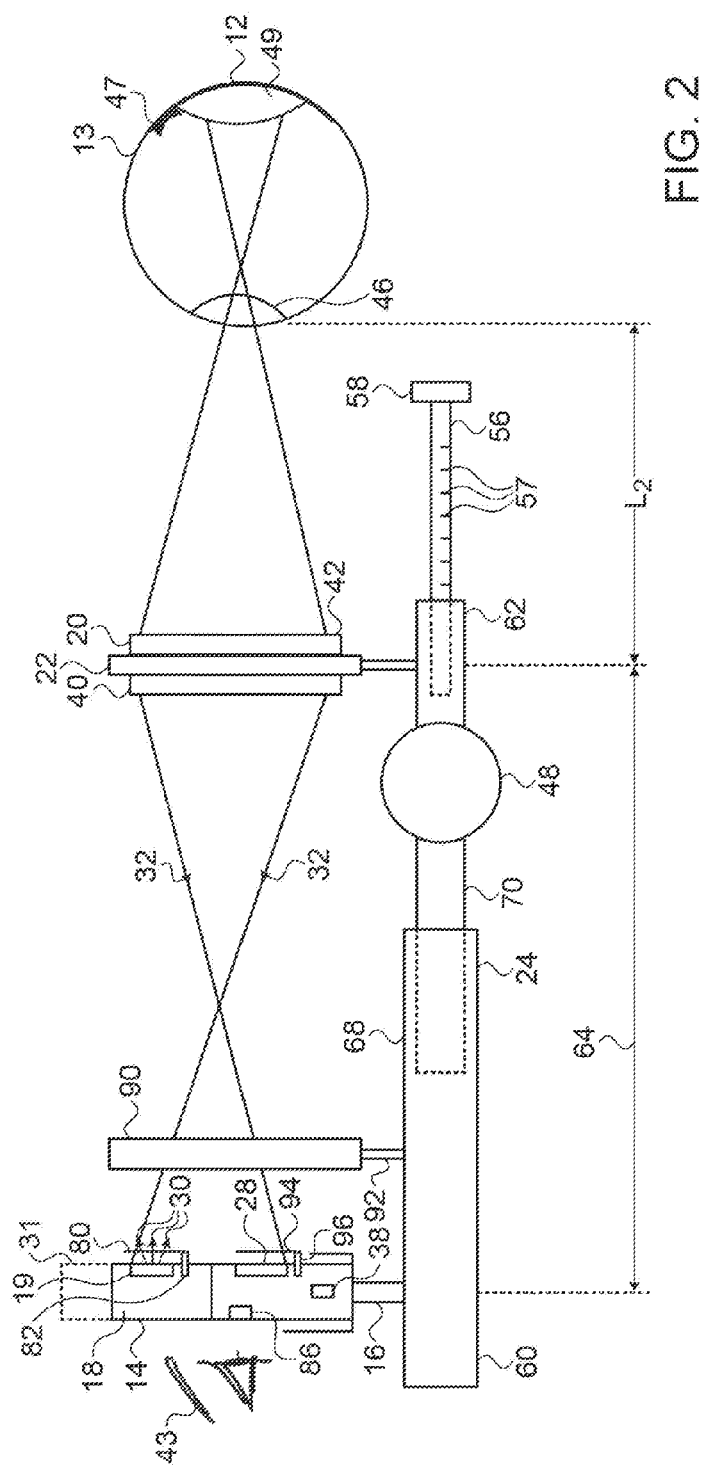
FIG. 2 schematically presents further details of the device for examining at least one eye portion of an eye of a subject, constructed and operative in accordance with an embodiment of the present invention.

Reference is now made to FIG. 2, which schematically presents further details of the device 10, constructed and operative in accordance with an embodiment of the present invention. The extendible support arm 24 includes, inter alia, a proximal end 60 and a distal end 62 and a distance 64 therebetween is adjustable by operating the adjusting unit 48, as described below.

The camera mounting unit 16 is attached to the extendible support arm 24 at the proximal end 60 and the adjustable lens holder 20 is attached to the extendible support arm 24 at the distal end 62. Typically, the extendible support arm 24 is telescopic and includes an outer sleeve 68 and an inner sleeve 70. The inner sleeve 70 slides telescopically in the outer sleeve 68, thereby enabling adjustment of the distance $L_1$ (FIG. 1). The first distance $L_1$ is adjusted in accordance with the medical requirements of the examination of the eye 13 by means of the adjusting unit 48, as described above.

In order to facilitate the examination of the at least one eye portion 12, a filter 80 is typically located in a filter holder 82, in proximity to the exit pupil 19 of the illuminating source 18. For example, in order to reduce the illuminating radiation intensity irradiating the at least one eye portion 12 and thus diminish the discomfort to the subject during the eye examination, a filter, such as a neutral density filter and/or a grey filter is selected for filter 80, as is known in the art.

Additionally or alternatively, in order to protect the ere from UV/IR radiation, which may be ,generated by the illuminating source 18, the filter 80 is selected as a UV/IR filter, as is known in the art.

Furthermore, for certain medical procedures, which require examination of the cornea, a blue filter is selected for the filter 80, is known in the art.

Moreover, for certain medical procedures, which require examination of different pathologies of the eye, a red-free filter is selected for the filter 80, as is known in the art.

In addition, in order to enhance the quality and contrast of the plurality of images generated by the camera 14, a polarizer 94 mounted on a polarizer holder 96 is positioned in front of the entrance pupil 28 of the camera 14, as is known in the art.

The extendible and retractable arm 56 is located at the distal end 62 of the extendible support arm 24 fir stabilizing, the abutment 5 against the forehead of the patient during the medical procedure, The extendible and retractable arm 56 includes, inter alia, a graduation scale 57 indicating to the user 43 a second distance $L_2$ of the abutment 58 from the first lens group 40. Typically, the extendible and retractable arm 56 is manually adjustable. It is appreciated that in some embodiments, the extendible and retractable arm 56 is adjustable by means of an appropriate motor, such as an electric motor.

In some embodiments, in order to magnify and clarify the observed area of interest 49, a second lens assembly 90 removably mounted on a second lens holder 92, removably attached to the extendible support arm 24, is located in proximity to the entrance pupil 26 of the camera 14. The second lens assembly 90 includes, inter alia, at least one magnifying lens for magnifying the reflected radiation 32, thereby increasing the sensitivity of the camera 14 to the area of interest 49.

Figure 3:
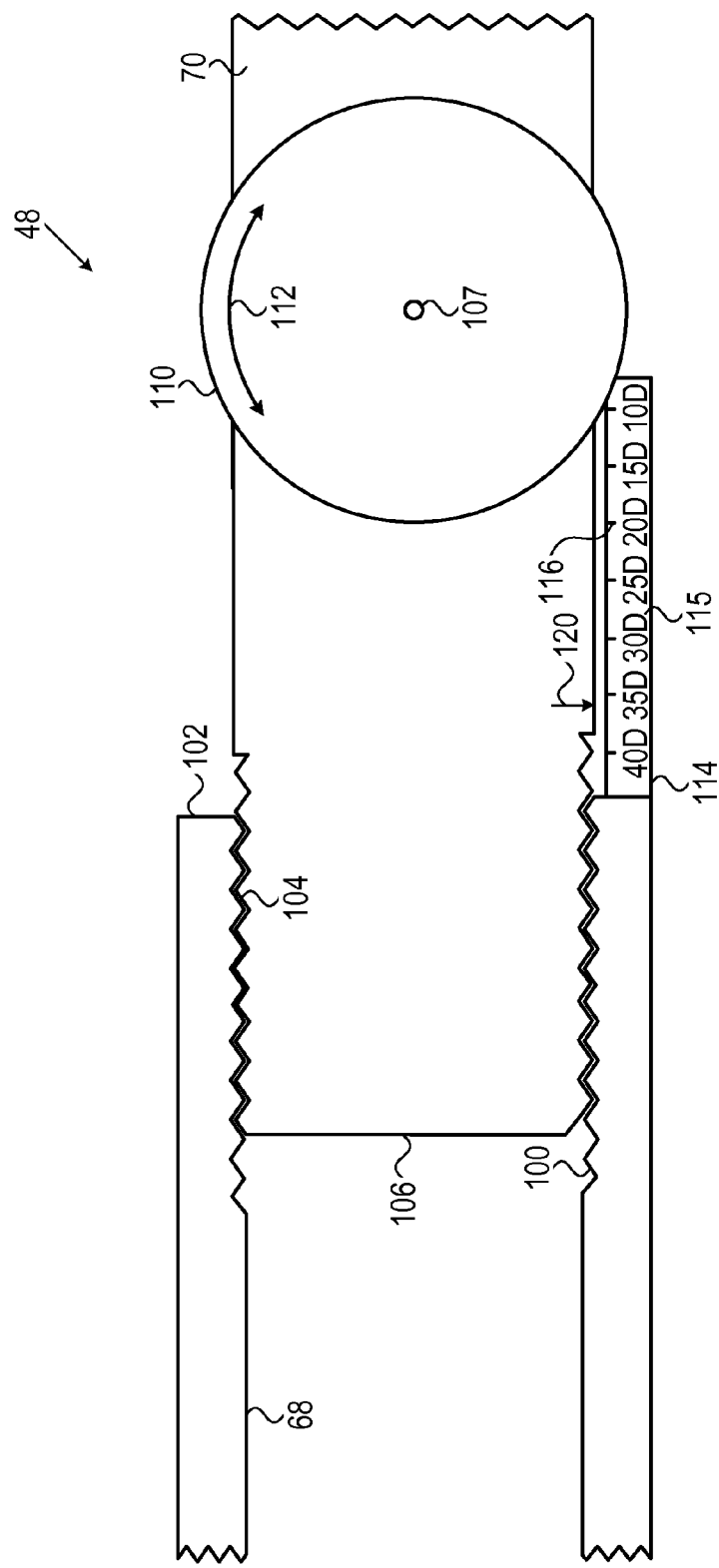
FIG. 3 schematically presents a cross-sectional view of the adjusting unit of the extendible support arm, constructed and operative in accordance with an embodiment of the present invention, and FIG. 4 schematically presents a cross-sectional view of the adjusting unit of the exendible support arm, constructed and operative in accordance with a further embodiment of the present invention.
Figure 4:
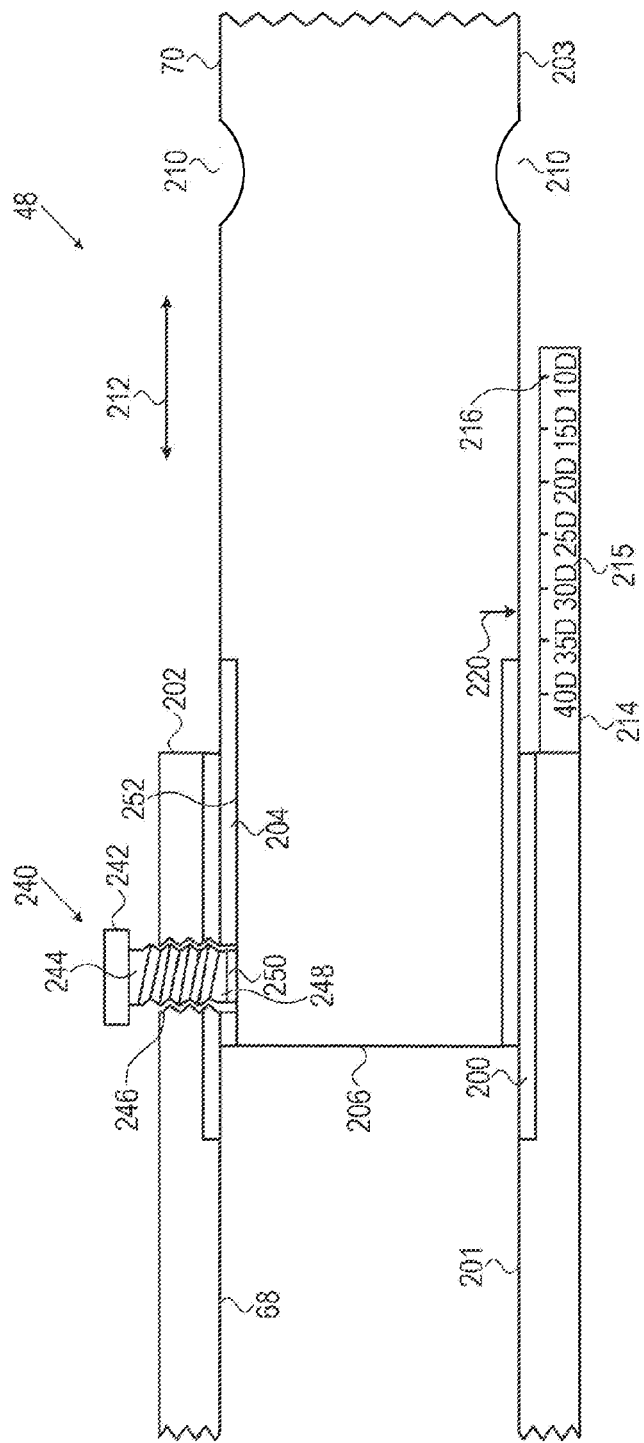

Reference is now made to FIG. 3, which schematically presents a cross-sectional view of the adjusting unit 48 of the extendible support 24, constructed and operative in accordance with an embodiment of the present invention. The adjusting unit 48 includes, inter alia, a set of geared teeth 100 located in proximity to an edge 102 of the outer sleeve 68. no inner sleeve 70 includes a corresponding set of geared teeth 104, engaging the set of geared teeth 100, is located, in proximity to an edge 106 of the inner sleeve 70. A control dial 110 is rotatablv attached to the inner sleeve 70 by means of an axle 107 and controls the lateral displacement of the inner sleeve 70 within the outer sleeve 68. By rotating the control dial 110. as indicated by a direction arrow 112, the user 43 adjusts the location of the inner sleeve 70 within the outer sleeve 68, thereby adjusting the distance $L_1$.

A diopter graduation scale 114 is located on the outer sleeve 68 and includes a graduated scale 115 including at least one mark 116. The graduated scale 115 indicates at least one diopter value of the lens assembly 20, for a corresponding first distance $L_1$. An indicating arrow 120 is included on the inner sleeve 70 and indicates to the user 43 the corresponding diopter mark of the first distance $L_1$.

It is appreciated that due to the camera properties, such as light sensitivity, and the eye being non-spherical, the user 43 may be required to finely adjust the first distance $L_1$ by rotating the dial 110, until the user 43 obtains a clear image of the area of interest 49.

Prior to the medical procedure, the user 43 determines the area of interest 49 of the eye 13, which requires observation and examination. Subsequently and prior to the observation and examination procedure, the user 43 decides on the diopter value of the lens assembly 20 and inserts the appropriate lens assembly 20 in the adjustable lens holder 22. The user adjusts the first distance $L_1$ by rotating the dial 48 until the arrow 120 indicates the required diopter mark on the scale 114. If required, the user 43 inserts the required filter 80 in the filter holder 82, as described above. By means of the extendible and retractable arm 56, the user 43 moves the arm 56 until the abutment end 58 abuts against the forehead of the patient, thereby stabilizing the device 10 during the medical procedure. The ophthalmoscope device 10 is located at the second distance $L_2$ from the pupil 46 of the eye 13. Typical values of $L_2$ are in a range of approximately 1 mm to 10 cms.

Reference is now made to HG. 4, which schematically presents a cross-sectional view of the adjusting unit 48 of the extendible support arm 24, constructed and operative in accordance with a further embodiment of the present invention. The adjusting unit 48 includes, inter alia, a coating 200, such as polytetrafluoroethylene (PTFE), coated on an inner surface 201 of the outer sleeve 68, in proximity to an edge 202 of the outer sleeve 68. The inner sleeve 70 includes a corresponding coating 204, polytetrafluoroethylene (PTFE), coated on an outer surface 203 of the inner sleeve 70, is in proximity to an edge 206 of the inner sleeve 70. The inner sleeve 70 frictionally engages the outer sleeve 68 by means of the coatings 200 and 204.

A diopter graduation scale 214 is located on the outer sleeve 68 and includes a graduated scale 215 including at least one mark 216. The graduated scale 215 indicates at least one diopter value of the lens assembly 20, for a corresponding first distance $L_1$. An indicating, arrow 220 is included on the inner sleeve 70 and indicates to the user 43 the corresponding diopter mark of the first distance $L_1$.

A securing unit 240 is attached to the adjusting unit 48 in order to secure the inner sleeve at the required first distance during the medical examination. The securing unit 240 includes, inter alia, a rotating, dial 242 having a threaded body 244, which moves in a threaded shaft 246 cut in the outer sleeve 68 and the coating 204. A distal end 248 of the threaded body 244 includes an abutment 250, typically constructed of polytetratluoroethylene (PTFE) material, which abuts against an outer surface 252 of the inner sleeve 70.

In order to adjust the first distance $L_1$, the user 43 grips the inner sleeve with his hands and manually displaces the inner sleeve 70 relative to the outer sleeve 68. At the required distance $L_1$, the user clamps the inner sleeve 70 within the outer sleeve 68 by rotating the dial 242 until the abutment 250 presses against the outer surface 252 of the inner sleeve 70.

It is appreciated that due to the camera properties, such as light sensitivity and the eye being non-spherical, the use 43 may be required to finely adjust the first distance $L_1$ by gripping a pair of finger depressions 210 and manually laterally displacing the inner sleeve 70 relative to the outer sleeve 68, until the user 43 obtains a clear image of the area of interest 49.

Prior to the medical procedure, the user 43 determines the area of interest 49 or the eye 13, which requires observation and examination. Subsequently and prior to the observation and examination procedure, the user 43 decides on the diopter value of the lens assembly 20 and inserts the appropriate lens assembly 20 in the adjustable lens holder 22. The user laterally adjusts the first distance $L_1$ by gripping in the inner sleeve 70 by means of the pair of finger depressions 210 and displacing the inner sleeve (as indicated by 212) until the arrow 220 indicates the required diopter mark on the scale 214. If required, the user 43 inserts the required filter 80 in the filter holder 82, as described above. By means of the extendible and retractable arm 56, the user 43 moves the arm 56 until the abutment end 58 abuts against the forehead of the patient, thereby stabilizing the device 10 during the medical procedure. The ophthalmoscope device 10 is located at the second distance L from the pupil 46 of the eye 13. Typical values of $L_2$ are in range of approximately 1 mm to 10 cms.

The user 43 observes the area of interest 49 through a viewing port 86 in the camera 14 (FIG. 2). The user 43 activates the illuminating source 18 and irradiates the at least one eye portion 12. The user 43 operates the camera 14 and generates the plurality of images of the at least one eye portion 12.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying, out this invention, but only by the claims that follow.

The invention claimed is:

1. A device for examining at least one selected portion of an eye of a subject, comprising:
    a camera detachably mourned on a camera mounting unit and including an illuminating source originating from the camera with a filter placed over the illuminating source, the illuminating source being operable to generate illuminating radiation for irradiating said at least one portion of the eye thereby enabling said camera to generate a plurality of images of said at least one portion of the eye;
    a first lens assembly detachably mounted on an adjustable lens holder and selected to focus said illuminating radiation awards said at least one portion of the eye and focus radiation reflected from said at least one portion of the eye towards an entrance pupil of said camera, and
    an extendible support arm having a proximal end and a distal end and being operable to support said camera mounting unit at said proximal end and said adjustable lens holder at said distal end at a first distance between said camera and said first lens assembly,
    wherein subsequent to adjusting said first distance to correspond to a diopter value of said selected first lens assembly, by means of an adjusting unit associated with said extendible support arm, said illuminating source is operably configured to irradiate said at least one portion of the eye and subsequent thereto said camera is operably configured to generate said plurality of images of the at least one portion of the eye.

2. The device for examining at least one portion of an eye according to claim 1, wherein said illumination source is located on a front panel of said camera.

3. The device for examining at least one portion of an eye according to claim 1, wherein said illumination source and the entrance pupil of said camera are located, within a field-of-view of said selected, first lens assembly.

4. The device for examining at least one portion of an eye according to claim 1, wherein said adjusting unit is configured to adjust said first distance.

5. The device for examining at least one portion of an eye according to claim 4, wherein said first distance is in a range of approximately 3 cms to 10 cms.

6. The device for examining at least one portion of an eye according to claim 4, wherein said extendible support arm comprises a telescopic support arm.

7. The device for examining at least one portion of an eye according to claim 1, wherein said first lens assembly comprises at least one focusing lens.

8. The device for examining at least one portion of an eye according to claim 1, wherein said diopter value is in a range of approximately 10 diopters to 40 diopters.

9. The device for examining at least one portion of an eye according to claim 1, wherein said selected first lens assembly has a diameter in a range of approximately 3 cms to 10 cms.

10. The device for examining at least one portion of an eye according to claim 1, further comprising a second lens assembly located in proximity to the entrance pupil of said camera and comprising at least one magnifying lens configured to magnify said reflected radiation.

11. The device for examining at least one portion of an eye according to claim 10, wherein said second lens assembly comprises at least one magnifying lens.

12. The device for examining at least one portion of an eye according to claim 1, wherein said camera is a portable camera.

13. The device for examining at least one portion of an eye according to claim 12, wherein said camera and said illuminating source are integrated in a mobile phone.

14. The device for examining at least one portion of an eye according to claim 1, wherein said camera includes a computer readable storage medium comprising a menu of instructions for operating said device, said menu of instructions comprises instructions fur performing all of the following functions:
   operating said illuminating source to irradiate said at least one portion of the eye;
   activating said camera to generate said plurality of images of said at least portion of the eye;
   comparing at least two eye images of said plurality of images for detecting eye changes in pathology of the eye;
   merging said at least two eye images of said plurality for detecting eye changes in pathology of the eye;
   storing said at least one image of said plurality of images.

15. The device for examining at least one portion of an eye according to claim 1, wherein said camera further comprises a storage area for storing subject information.

16. The device for examining at least one portion of an eye according to claim 1, further comprising an extendible and retractable arm integrally located in said extendible support arm and configured to stabilize said device against the subject during a medical procedure.

17. The device for examining at least one portion of an eye according to claim 6, wherein said adjusting unit comprises:
   an outer sleeve having a first set of geared teeth associated with an inner surface of said outer sleeve;
   an inner sleeve having a second set of geared teeth associated with an outer surface of said inner sleeve and said second set of geared teeth is configured to engage said first set of geared teeth, and
   a dial rotatably attached to said inner sleeve,
   wherein said dial is operably configured to displace said inner sleeve within said outer sleeve by said first set of geared teeth engaging said second set of geared teeth, such that said adjusting unit adjusts said first distance.

18. The device for examining at least one portion of an eye according to claim 6, wherein said adjusting unit comprises:
   an outer sleeve having a first frictional coating associated with an inner surface of said outer sleeve;
   an inner sleeve having a second frictional coating associated with an outer surface of said inner sleeve and said second frictional coating is configured to frictionally engage said first frictional coating, and
   a securing unit configured to secure said inner sleeve within said outer sleeve,
   wherein upon manually displacing said inner sleeve within said outer sleeve by said frictional engagement between said first frictional coating and said second frictional coating, said adjusting unit adjusts said first distance and said securing unit is configured to secure said inner sleeve at said first distance.

19. The device for examining at least one portion of an eye according to claim 1, wherein said camera further comprises a viewing port for observing an area of interest in the subjects eye.

* * * * *